United States Patent [19]

Toyoshima et al.

[11] Patent Number: 4,650,785

[45] Date of Patent: Mar. 17, 1987

[54] PHARMACEUTICAL COMPOSITION HAVING AN EXCELLENT ABSORPTION PROPERTY

[75] Inventors: Shigeshi Toyoshima; Yoshiko Seto, both of Funabashi; Koji Fukushima, Tama; Izumi Kumashiro, Yokohama, all of Japan

[73] Assignee: Ajinomoto Company Incoporated, Tokyo, Japan

[21] Appl. No.: 690,839

[22] Filed: Jan. 14, 1985

Related U.S. Application Data

[63] Continuation of Ser. No. 489,269, Apr. 27, 1983, abandoned.

[30] Foreign Application Priority Data

Apr. 30, 1982 [JP] Japan .................................... 73306

[51] Int. Cl.$^4$ ............................................. A61K 37/26
[52] U.S. Cl. ........................................... 514/3; 514/12
[58] Field of Search ..................... 514/3, 946; 562/443, 562/449

[56] References Cited

U.S. PATENT DOCUMENTS 4,261,919 4/1981 Knowles et al. .................... 562/443
4,380,646 4/1983 Franzmann ......................... 548/502

FOREIGN PATENT DOCUMENTS 2553689 10/1976 Fed. Rep. of Germany ...... 562/445
49-4210 10/1974 Japan ................................. 562/445
161121 5/1982 Japan ........................... 424/DIG. 15
030688 9/1982 Japan ........................... 424/DIG. 15

OTHER PUBLICATIONS

*Israel Journal of Chemistry*, vol. 12, No. 3, pp. 757–763 (1974) (Lustig et al).

Primary Examiner—Frederick E. Waddell
Attorney, Agent, or Firm—Oblon, Fisher, Spivak, McClelland & Maier

[57] ABSTRACT

A compound represented by the formula:

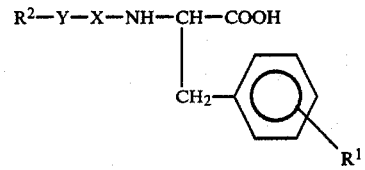

wherein $R^1$ is a hydrogen atom, a fluorine atom, a nitro group, a hydroxyl group or a hydroxyl group protected by an esterifying group; X is CO or $SO_2$; —Y— is a straight bond, a lower alkylene group, a substituted or unsubstituted vinylene group, or group having the formula —$CH_2$—O— or —O—$CH_2$—; $R^2$ is a substituted or unsubstituted phenyl or naphthyl group, or $R^2$—Y—CO is N-benzyloxycarbonylphenylalanyl, N-benzyloxycarbonyl-4-fluorophenylalanyl or N-(m-methoxycinnamoyl)-phenylalanyl group; or a non-toxic salt thereof is disclosed along with pharmaceutical compositions containing these compounds and methods of using these compositions to increase the rate of absorption of medicines.

20 Claims, No Drawings

PHARMACEUTICAL COMPOSITION HAVING AN EXCELLENT ABSORPTION PROPERTY

This application is a continuation of application Ser. No. 489,269, filed Apr. 27, 1983 now abandoned.

The present invention relates to a novel pharmaceutical composition or preparation comprising at least a phenylalanine derivative as an excellent absorption promoter, and a medicine. Thereby, the absorption of the medicine can be improved excellently in the oral or rectal administration.

The phenylalanine derivative is a compound represented by general formula (I):

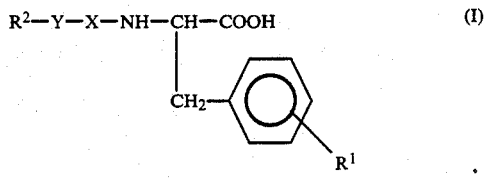

wherein $R^1$ is a hydrogen atom, a fluorine atom, a nitro group, a hydroxyl group or a hydroxyl group protected by an esterifying group; X is CO or $SO_2$; —Y— is a straight bond, a lower alkylene group, a substituted or unsubstituted vinylene group, or a group having the formula —$CH_2$—O— or —O—$CH_2$; $R^2$ is a substituted or unsubstituted phenyl or naphthyl groups, or $R^2$—Y—CO— is an N-benzyloxycarbonylphenylalanyl, N-benzyloxycarbonyl-4-fluorophenylalanyl, or N-(m-methoxycinnamoyl)phenylalanyl group; or a nontoxic salt thereof.

An example of the hydroxyl group protected by an esterifying group is a benzyloxycarbonyl group. Examples of group $R^2$ include phenyl and naphthyl groups which may have a halogen atom such as chlorine or fluorine atom, a nitro group, a lower alkyl group such as methyl, trifluoromethyl, or a lower alkyloxy group such as methoxy as a substituent.

The compounds having formula (I) are unique in that they can be used as a medicine absorption promoter. Phenylalanine per se, or N-acetylphenylalanine or lower alkyl esters or amides of the acids of formula (I) are not useful as the absorption promoter. The compounds of formula (I) have asymmetric carbon atoms and may take on a D-form, L-form or a DL-form depending upon the specific combination of substituents. The phenylalanine derivatives used for the present invention are known or novel, and can be prepared by conventional N-acylation techniques.

The phenylalanine derivatives of the present invention may be in a form of a salt, such as a metal salt, for example, sodium, potassium, lithium, and calcium salts, and a salt with an organic base which are pharmaceutically acceptable. As the organic base, there can be adopted amines such as ammonia (ammonium salt), dicyclohexylamine, and N-methyl-D-glucamine, and basic amino acids such as lysine and arginine.

The phenylalanine derivative in the present invention is administered orally or rectally together with the medicine. In the case of insulin, it not only promotes the absorption of insulin but also inhibits the degradation of insulin in the presence of trypsin and chymotrypsin.

Particularly, oral or rectal administration of insulin for the treatment of diabetes mellitus has not been clinically established yet, and the development of an insulin-absorption promoter that permits extended and convenient use for humans is needed.

The medicine is, for example, one from the polypeptides, their deviatives, or an analogue of these compounds, which have two or more hydrophobic amino acid residues being close to each other or in a cluster at one or more regions so that the residues interact noncovalently with the hydrophobic portions of the adjuvant. Examples include a soluble globular protein having a cluster or clusters of hydrophobic amino acid residues on the surface such as insulin, insulin-like growth factor I, insulin-like growth factor II, pancreatic polypeptide, a cyclic peptide having two or more hydrophobic amino acid residues being close to each other or in a cluster such as cyclic peptide hormones, and the preferred conformation, which is induced by the presence of the adjuvant from a random coil or other forms of the polypeptide and its derivatives and their analogues, and has two or more hydrophobic amino acid residues being close to each other or in a cluster at one or more regions such as peptide hormones and effectors.

The absorption promoter of the present invention (the phenylalanine derivative) may be employed in the range of from 0.1-2,000 mg preferably 0.2-500 mg or 25 U of the medicine, for example, insulin.

The absorption promoter may be administered in the composition form with the medicine.

Regarding the composition form, the phenylalanine derviative can be used by formulating it into preparations such as tablets, capsules, and elixirs solutions, suspensions, etc.

The phenylalanine derviative and the medicine such as insulin can be administered to a subject requiring such treatment (humans) in a dosage range of 0.1-1,000 mg per subject generally several times a day, that is, in a total daily dosage of 0.2-2,000 mg. The dosage varies according to the seriousness of disease, the body weight of subjects, and other factors acknowledged by those skilled in the art.

The foregoing typical combinations of drug are formulated into pharmaceutical compositions stated below. About 0.2-500 mg of the phenylalanine derivative and the medicine such as insulin are blended into unit dosage forms generally acknowledged or required for the pharmaceutical practice together with pharmaceutically acceptable vehicles, carriers, excipients, binders, antiseptics, stabilizers, flavorings, and so forth. The amount of each active substance in these compositions or preparations is adjusted in such a way as to give an appropriate dosage of the prescribed range.

Specific materials which can be incorporated into tablets, capsules, and so forth are as follows: A binder such as traganth, gum arabic, cornstarch, and gelatin; an excipient such as microcrystalline cellulose; a swelling agent such as cornstarch, pregelatinized starch, and arginic acid; a lubricant such as magnesium stearate; a sweetener such as sucrose, lactose and saccharin; a flavoring such as peppermint, an oil from Gaultheria adenothrix Maxim, and cherry. Enteric coating may be favorably used. For example, hydroxyphenylmethylcellulose (8%) aqueous solution as pre-coating agent for undercoat and hydroxypropylmethylcellulose phthlate (10%) and polyacetyne (3%) aqueous solution as coating agent are used. When the unit dosage form of the preparation is a capsule, a liquid carrier such as fatty oil can further be incorporated in the foregoing type materials. Various other materials can be present as a coating material or in order to vary the physical form of unit dosage forms according to other methods. For example, tablets can be coated with shellac and/or sugar. Syrups or elixirs can contain active compounds, sucrose as a sweetener, methyl- and propylparaben as an antiseptic, a coloring matter, a flavoring such as cherry and an orange flavoring.

Aseptic compositions can be formulated according to the usual practice for preparation of pharmaceutical dosage forms, in which practice an active substance is dissolved or suspended in a vehicle such as water.

A buffer, antiseptic, and an antioxidant can further be incorporated as occasion demands.

The examples for preparation of the compounds used for the active ingredient of the present invention will be shown as follows:

EXAMPLE FOR PREPARATION 1

Production of "S-6"

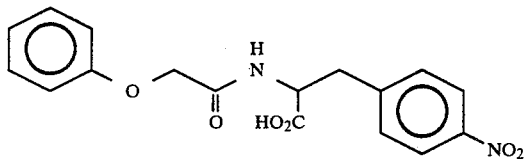

4-Nitro-L-phenylalanine (21 g) was dissolved in 10% NaOH (10 ml), and an ethyl ether solution of phenoxyacetyl chloride (1.7 g) and an aqueous $Na_2CO_3$ solution prepared from $Na_2CO_3$ 2.7 g and water 25 ml were alternately added stepwise thereto while stirring at room temperature over 20 minutes. After that, the mixture was stirred at a room temperature for 3 hours, and then acidified with dilute HCl to precipitate the crystals. The crystals were filtered, washed with water, and re-crystallized from dioxan to obtain N-phenoxyacetyl-4-nitro-L-phenylalanine as needles having melting point: 147° C. (2.4 g).

Elementary analysis: Calc. C 59.30%, H 4.68%, N 8.14%. Found: C 59.47%, H 4.51%, N 8.03%.

EXAMPLE FOR PREPARATION 2

Production of "S-8"

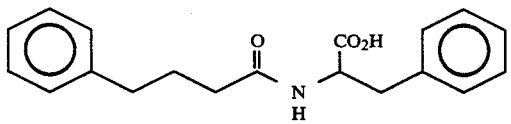

4-phenylbutyric acid (25 g) was dissolved in chloroform (500 ml), and N-hydroxysuccinimide (17.3 g) was added thereto. N,N'-dicyclohexylcarbodiimide (31 g) was added in some portions to the above mixture with ice-cooling while stirring. The mixture was stirred for 1 hour under cooling and then for 7 hours at room temperature. After an addition of glacial acetic acid (10 ml), the mixture was stirred for 1 hour, the insoluble matter was removed by filtration and the filtrate was evaporated to dryness under reduced pressure. The residue was allowed to recrystallize from ethyl acetate to obtain 4-phenylbutyric acid N-hydroxysuccinimide ester (35 g) having melting point: 82° C.

The above mentioned ester (13 g) was dissolved in chloroform (200 ml). This solution was added dropwise to the solution obtained by dissolving L-phenylalanine (16.5 g) and $Na_2CO_3$ (15.9 g) in water (150 ml) while stirring at room temperature. After that, the mixture was stirred for 7 hours and the insoluble matter thus produced was removed by filtration. The filtrate was acidified to pH 1.0 with 6N HCl. The precipitated crystals were filtered, washed with water, and re-crystallized from 90% aqueous methanol to obtain N-(4-phenylbutyroyl)-L-phenylalanine (11.2 g) having melting point: 178° C.

Elementary analysis: Calc. C 73.28%, H 6.79%, N 4.49%. Found C 73.24%, H 6.94%, N 4.46%.

Optical rotation: $[\alpha]_D^{26} = +8.33°$ (C=1, acetone).

In the same manner as above, the following products as listed were obtained:

| Product | Molecular Formula | m.p. (°C.) | Optical rotation |
|---|---|---|---|
| S-24 | $C_{18}H_{16}ClNO_3$ | 155-158 | $[\alpha]_D^{30} - 31.02°$ (C = 1, MeOH) |
| 25 | $C_{18}H_{16}ClNO_3$ | 157-159 | $[\alpha]_D^{30} + 31.20°$ (C = 1, MeOH) |
| 27 | $C_{19}H_{19}NO_3$ | 135-140 | $[\alpha]_D^{25} - 35.89°$ (C = 1, MeOH) |
| 30 | $C_{19}H_{16}F_3NO_3$ | 158-160 | $[\alpha]_D^{20} - 19.10°$ (C = 1, MeOH) |
| 31 | $C_{18}H_{16}FNO_3$ | 145-148 | $[\alpha]_D^{20} - 50.98°$ (C = 1, MeOH) |
| 36 | $C_{19}H_{16}F_3NO_3$ | 157-160 | $[\alpha]_D^{20} + 19.03°$ (C = 1, MeOH) |

EXAMPLE FOR PREPARATION 3

Production of "S-11"

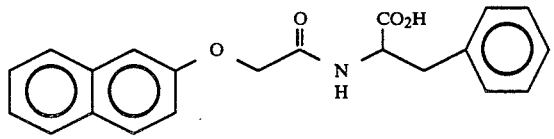

L-Phenylalanine (0.1 mole) was dissolved in 2N-NaOH (50 ml) and ethyl ether (20 ml) was added thereto. To the mixture while stirring vigorously with ice-cooling the desired naphthoxyacetyl chloride (0.1 mole) and 2N-NaOH (100 ml) in small portions were added. The mixture was stirred for 3 hours at room temperature and washed once with ethyl ether. The aqueous layer was adjusted to pH 2 with 4N-HCl to precipitate crude crystals. The crystals were placed on a filter paper, dried and re-crystallized from ethylacetate-petroleum ether. Compound "S-12" was produced in the same manner as above. The results were obtained as follows:

TABLE 1

| Product | Melting Point (°C.) | $[\alpha]_D^{20}$ (C = 1, methanol) | Yield on Purified Crystal (%) |
|---|---|---|---|
| N—[(1-naphthoxy)acetyl]-L-phenylalanine (S-11) | 137-142 | −10.6° | 33 |
| N—[(2-naphthoxy)acetyl]-L-phenylalanine (S-12) | 173-176 | +25.1° | 36 |

EXAMPLE FOR PREPARATION 4

Production of "S-21", Z-Phe$^L$-Phe$^D$

D-Phenylalanine (17.3 g) and NaHCO$_3$ (17.6 g) were added to water (150 ml).

N-Benzyloxycarbonyl-L-phenylalanine N-hydroxysuccinimide ester (27.7 g) was dissolved in tetrahydrofuran (150 ml) and the thus obtained solution was added to the above aqueous solution at room temperature. The mixture was reacted overnight. To the reaction mixture, water (200 ml) was added and then the aqueous phase was adjusted to pH 2 with cooled 4N-HCl. The desired product was extracted with ethyl acetate (500 ml). The organic layer was washed with 1N HCl, and saturated aqueous NaCl solution, in order, and dried over anhydrous magnesium sulfate. The solution was evaporated to dryness under reduced pressure. Thus obtained residue (28.0 g) was re-crystallized from ethyl acetate-n-hexane to obtain the object product (20.3 g, yield: 65%).

In the same manner as above, "S-22", "S-23" and "S-32" were obtained.

| Product | | m.p. (°C.) | Optical Rotation |
|---|---|---|---|
| S-21 | C$_{26}$H$_{26}$N$_2$O$_5$ | 119–125 | $[\alpha]_D^{17} = -34.2°$ (C = 1, EtOH) |
| S-22 | C$_{26}$H$_{25}$FN$_2$O$_5$ | 158–163 | $[\alpha]_D^{23} = +13.9°$ (C = 1, EtOH) |
| S-23 | C$_{26}$H$_{25}$FN$_2$O$_5$ | 133–135 | $[\alpha]_D^{23} = -19.5°$ |
| S-32 | C$_{28}$H$_{28}$N$_2$O$_5$ | 189–191 | (C = 1, EtOH) $[\alpha]_D^{22} = -24.0°$ (C = 1, DMF) |

The present invention is hereunder described in greater detail by reference to examples and laboratory tests, which are given here for illustrative purposes only and are by no means intended to limit the scope of the invention.

EXAMPLES AND LABORATORY TESTS

The absorption promoter samples listed in Table 2 were dissolved or suspended in 0.5% CMC-0.05M tris-HCl buffers (pH: 7.8) and the solutions or suspensions were mixed with aqueous insulin solution. Female ICR-CD-1 mice 5 to 7 weeks old were orally administered predetermined amounts of the mixtures. A predetermined duration later, the percent decrease in blood glucose and the degree of elevation of blood insulin as compared with the control group were measured. The results are shown in Table 2. The symbol "Z" in the structural formulas in the table represents a benzyloxycarbonyl group. The upper figures in the columns "effectiveness" represent the percent decrease in blood glucose and the lower parenthesized figures indicate the degree of elevation in blood insulin.

TABLE 2

| Sample No. | Structure | Dose with Insulin 2.5 U/10 g (Body Weight) | (1) Decrease in Blood Glucose (%) (2) Degree of Elevation of Blood Insulin Time (minutes) 30 | 60 |
|---|---|---|---|---|
| S-1 | (1-naphthyl)-CH$_2$-CO-Phe$^L$ | 6.0 mg/10 g | 84.9 (56.4) | 75.4 (60.0) |
| S-2 | O$_2$N-C$_6$H$_4$-O-CH$_2$-CO-NH-CH(CO$_2$H)-CH$_2$-C$_6$H$_4$-NO$_2$ (DL–) | 6.0 mg/10 g | 23.2 (>119) | 60.0 (89.7) |
| S-3 | C$_6$H$_5$-CH=CH-CO-Phe$^L$ | 6.0 mg/10 g | 84.4 (34.2) | 84.3 (68.1) |
| S-4 | Z-HN-CH(CO$_2$H)-CH$_2$-C$_6$H$_4$-O-Z (L–) | 3.0 mg/10 g | 52.7 (6.54) | 31.1 (2.04) |

TABLE 2-continued

| Sample No. | Structure | Dose with Insulin 2.5 U/10 g (Body Weight) | (1) Decrease in Blood Glucose (%) (2) Degree of Elevation of Blood Insulin Time (minutes) | |
|---|---|---|---|---|
| | | | 30 | 60 |
| S-5 | C₆H₅-O-CH₂-C(=O)-Phe-L | 12.5 mg/10 g | 57.9 (88.5) | 33.5 (18.0) |
| S-6 | C₆H₅-O-CH₂-C(=O)-NH-CH(CO₂H)-CH₂-C₆H₄-NO₂ (L—) | 3.1 mg/10 g | 21.5 (20.6) | 44.7 (21.8) |
| S-7 | Z—Phe—Phe (L, L) | 3.0 mg/10 g | 70.0 (7.72) | 40.6 (9.35) |
| S-8 | C₆H₅-(CH₂)₃-C(=O)-Phe-L | 6.0 mg/10 g | 57.1 (7.31) | 35.6 (9.64) |
| S-9 | C₆H₅-O-CH₂-C(=O)-Phe-D | 3.0 mg/10 g | 37.3 (11.8) | 29.7 (2.67) |
| S-10 | Z—Phe—Tye (L, L) | 6.0 mg/10 g | 61.5 (41.9) | 43.4 (4.85) |
| S-11 | 1-Naphthyl-O-CH₂-C(=O)-Phe-L | 6.0 mg/10 g | 54.0 (11.8) | 59.7 (5.07) |
| S-12 | 2-Naphthyl-O-CH₂-C(=O)-Phe-L | 6.0 mg/10 g | 50.8 (6.05) | 66.8 (5.62) |
| S-13 | 4-Cl-C₆H₄-O-CH₂-C(=O)-Phe-L | 1.5 mg/10 g | 31.9 (43.4) | 18.5 (9.82) |
| S-14 | C₆H₅-C(=O)-Phe-L | 6.0 mg/10 g | 35.2 (6.31) | 37.8 (3.31) |
| S-15 | Z—Phe-L | 3.0 mg/10 g | 37.5 (3.43) | 60.7 (2.36) |

TABLE 2-continued
| Sample No. | Structure | Dose with Insulin 2.5 U/10 g (Body Weight) | (1) Decrease in Blood Glucose (%) (2) Degree of Elevation of Blood Insulin Time (minutes) 30 | 60 |
|---|---|---|---|---|
| S-16 | L<br>Z—Tyr | 6.0 mg/10 g | 31.0 (50.0) | 27.2 (2.99) |
| S-17 | 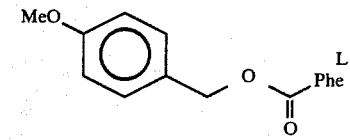 | 3.0 mg/10 g | 64.8 (14.4) | 50.6 (21.2) |
| S-18 | D<br>Z—Phe | 6.0 mg/10 g | 52.3 (6.79) | 67.2 (10.6) |
| S-20 | D  L<br>Z—Phe—Phe | 1.5 mg/10 g | 22.4 (2.33) | 32.7 (2.46) |
| S-21 | L  D<br>Z—Phe—Phe | 6.0 mg/10 g | 42.6 (14.9) | 32.7 (5.26) |
| S-22 | 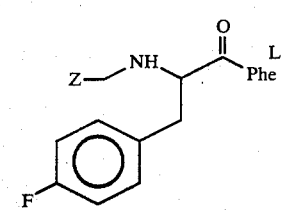 | 3.0 mg/10 g | 63.7 (—) | 51.9 (—) |
| S-23 | 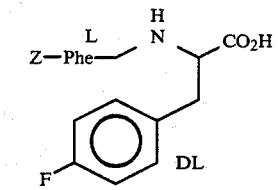 | 3.0 mg/10 g | 67.5 (—) | 39.4 (—) |
| S-24 | 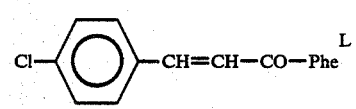 | 1.5 mg/10 g | 37.1 (5.46) | 27.4 (3.04) |
| S-25 | 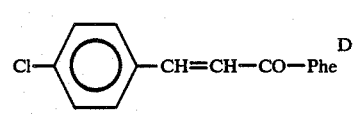 | 1.5 mg/10 g | 34.9 (—) | 29.5 (—) |
| S-27 | 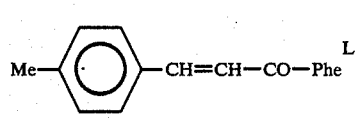 | 1.5 mg/10 g | 61.5 (7.76) | 34.4 (1.0) |
| S-30 | 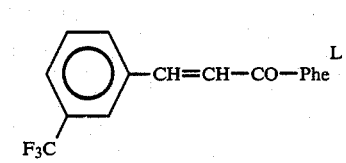 | 3.0 mg/10 g | 48.8 (—) | 44.4 (—) |
| S-31 | 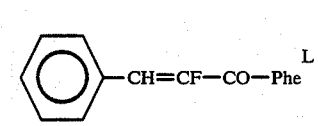 | 3.0 mg/10 g | 33.5 (—) | 72.5 (—) |

TABLE 2-continued

| Sample No. | Structure | Dose with Insulin 2.5 U/10 g (Body Weight) | (1) Decrease in Blood Glucose (%) (2) Degree of Elevation of Blood Insulin Time (minutes) | |
|---|---|---|---|---|
| | | | 30 | 60 |
| S-32 | 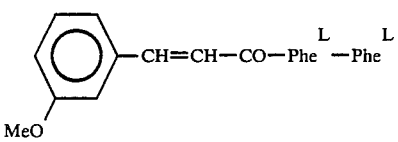 MeO-C₆H₄-CH=CH-CO-Phe L -Phe L | 3.0 mg/10 g | — (—) | 23.8 (4.55) |
| S-33 | TS—Phe L | 6.0 mg/10 g | 51.6 (18.1) | 21.4 (6.48) |
| S-34 | Ts—Phe DL | 6.0 mg/10 g | 27.3 (13.8) | 93.1 (6.52) |
| S-36 |  F₃C-C₆H₄-CH=CH-CO-PHe D | 3.0 mg/10 g | 52.0 (—) | 49.1 (—) |

Some Samples used for present invention are as follows:

S-1: N-[(1-naphthyl)acetyl]-L-phenylalanine,
S-2: N-[(4-nitrophenoxy)acetyl]-4-nitro-DL-phenylalanine
S-3: N-cinnamoyl-L-phenylalanine,
S-4: N,O-bis-(benzyloxycarbonyl)-L-tyrosine
S-5: N-phenoxyacetyl-L-phenylalanine
S-6: N-phenoxyacetyl-4-nitro-L-phenylalanine
S-7: N-benzyloxycarbonyl-L-phenylalanyl-L-phenylalanine
S-8: N-(4-phenylbutyrol)-L-phenylalanine
S-9: N-phenoxyacetyl-D-phenylalanine
S-10: N-benzyloxycarbonyl-L-phenylalanyl-L-tyrosine
S-11: N-[(1-naphthoxy)acetyl]-L-phenylalanine
S-12: N-[(2-naphthoxy)acetyl]-L-phenylalanine
S-13: N-[(4-chlorophenoxy)acetyl]-L-phenylalanine
S-14: N-benzoyl-L-phenylalanine
S-15: N-benzyloxycarbonyl-L-phenylalanine
S-16: N-benzyloxycarbonyl-L-tyrosine
S-17: N-(4-methoxybenzyloxycarbonyl)-L-phenylalanine
S-18: N-benzyloxycarbonyl-D-phenylalanine
S-19: N-(4-fluorobenzyloxycarbonyl)-L-phenylalanine
S-20: N-benzyloxycarbonyl-D-phenylalanyl-L-phenylalanine
S-21: N-benzyloxycarbonyl-L-phenylalanyl-D-phenylalanine
S-22: N-benzyloxycarbonyl-4-fluoro-DL-phenylalanyl-L-phenylalanine
S-23: N-benzyloxycarbonyl-L-phenylalanyl-4-fluoro-DL-phenylalanine
S-24: N-(4-chlorocinnamoyl)-L-phenylalanine
S-25: N-(4-chlorocinnamoyl)-D-phenylalanine
S-26: N-(4-fluorocinnamoyl)-L-phenylalanine
S-27: N-(4-methylcinnamoyl)-L-phenylalanine
S-28: N-(4-trifluoromethylcinnamoyl)-L-phenylalanine
S-29: N-(3-methoxycinnamoyl)-L-phenylalanine
S-30: N-(3-trifluoromethylcinnamoyl)-L-phenylalanine
S-31: N-(α-fluorocinnamoyl)-L-phenylalanine
S-32: N-(3-methoxycinnamoyl)-L-phenylalanyl-L-phenylalanine
S-33: N-(4-toluenesulfonyl)-L-phenylalanine
S-34: N-(4-toluenesulfonyl)-DL-phenylalanine
S-35: N-(4-trifluoromethylcinnamoyl)-D-phenylalanine
S-36: N-(3-trifluoromethylcinnamoyl)-D-phenylalanine Table 2 shows the effectiveness of the absorption promoter of the present invention when it was administered orally, but it should be understood that the same results are obtained by using the absorption promoter as a conventional suppository preparation together with insulin.

As described in the foregoing, the absorption promoter of the present invention is very useful in that it enables clinical insulin therapy by the oral or parenteral (e.g. rectal) route.

Toxicity Studies of Phenylalanine Derivatives with Oral IN Potentiating Activity in Female CD-1(ICR) Mice are as follows:

| Chemical structures of amino acid derivatives | LD$_{50}$ (mg/kg) |
|---|---|
| N—Phenoxyacetyl-L-phenylalanine | >4,000 |
| N—(1-Naphthyloxy)acetyl-L-phenylalanine | >4,000 |
| N—(2-Naphthyloxy)acetyl-L-phenylalanine | >4,000 |
| N—(4-Chlorophenoxy)acetyl-L-phenylalanine | >3,500 |
| N—Benzyloxycarbonyl-L-phenylalanine | >2,750 |
| N—Benzyloxycarbonyl-D-phenylalanine | >4,000 |
| N—p-Methoxybenzyloxycarbonyl-L-phenylalanine | 750 |
| N—Benzyloxycarbonyl-L-phenylalanyl-L-phenylalanine | >3,000 |
| N—Benzyloxycarbonyl-L-phenylalanyl-L-tyrosine | >3,000 |
| N—Cinnamoyl-L-phenylalanine | >2,500 |

Phenylalanine derivatives were suspended in 0.5% CMC.

EXAMPLE FOR TABLET

Porcine insulin (0.577 g, 15,000 U, Zn content 0.5%) was dissolved in 0.05N HCl (30 ml) and the thus obtained solution was diluted with distilled water (30 ml).

A compound "S-27" (6 g) was dissolved in 0.1N HaOH (200 ml) and the pH value was adjusted to 7.5 by the addition of 0.1N HCl. The solution was diluted with phosphate buffer (0.02M, pH 7.5) to the volume of 600 ml.

The insulin solution as produced above was added dropwise to the S-27 solution maintained at 20° C. while vigorously stirring, the solution was adjusted to pH 7.5, and immediately was freeze-dried.

There were prepared tablets containing the freeze-dried material (25 mg), with pregelatinized starch (82 mg), microcrystalline cellulose (82 mg), and magnesium stearate (1 mg). Enteric coating tablets are prepared by the conventional methods using hydroxyphenylmethylcellulose (8%) aqueous solution as pre-coating agent for undercoat and hydroxypropylmethylcellulose phthalate (10%) and polyacetyne (3%) aqueous solution as coating agent.

EXAMPLE FOR CAPSULE

To glacial acetic acid (250 ml), a compound "S-22" (30 g) was added and dissolved by heating. Porcine insulin (2 g, 52,200 U, Zn content: 0.5%) was added in small portions to the above solution cooled at 20° C. while stirring and dissolved. From the solution the acetic acid was distilled off under reduced pressure at the same temperature.

To thus obtained solid residue, n-hexane (100 ml) was added and the solid residue was pulverized, then obtained on a filter, and washed with n-hexane. n-Hexane adhered to the powder was evaporated under reduced pressures. The powder was dried under reduced pressures in the presence of solid NaOH.

Dry packed capsules containing 50 mg/capsule of an active ingredient were prepared.

| | |
|---|---|
| the above powder | 50 mg |
| Lactose | 149 mg |
| Magnesium stearate | 1 mg |
| Capsule | 200 mg |

The powder was reduced to a No. 60 powder. Lactose and magnesium stearate were passed through a No. 60 sieve cloth to fall over the foregoing powder and mixed sufficiently with it. The mixture was packed into No. 1 dry gelatin capsules.

What is claimed is:

1. An orally administratable pharmaceutical composition in dosage unit form suitable for gastrointestinal absorption, comprising a mixture of insulin, and an adjuvant having the formula:

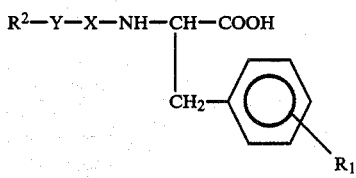

wherein $R^1$ is a hydrogen atom, a fluorine atom, a nitro group, a hydroxyl group or a hydroxyl group protected by an esterifying group; X is CO or $SO_2$; —Y— is a straight bond, a lower alkylene group, a substituted or unsubstituted vinylene group, or a group having the formula —$CH_2$—O— or —O—$CH_2$—; and $R^2$ is a substituted or unsubstituted phenyl or naphthyl group; or a nontoxic salt thereof.

2. An orally administratable pharmaceutical composition in dosage unit form suitable for gastrointestinal absorption, comprising a mixture of insulin, and an adjuvant having the formula:

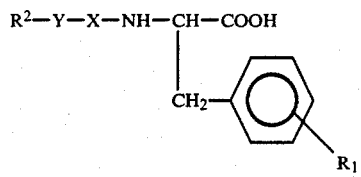

wherein $R^1$ is a hydrogen atom, a fluorine atom, a nitro group, a hydroxyl group or a hydroxyl group protected by an esterifying group; and $R^2$—Y—X is an N-benzyloxycarbonyl-phenylalanyl, an N-benzyloxycarbonyl-4-fluoro-phenylalanyl, or an N-(m-methoxycinnamoyl)-phenylalanyl group; or a nontoxic salt thereof.

3. A method of promoting the oral absorption of insulin, which comprises orally administering concurrently with insulin an adjuvant of the formula:

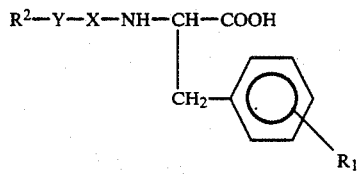

wherein $R^1$ is a hydrogen atom, a fluorine atom, a nitro group, a hydroxyl group or a hydroxyl group protected by an esterifying group; X is CO or $SO_2$; —Y— is a straight bond, a lower alkylene group, a substituted or unsubstituted vinylene group, or a group having the formula —$CH_2$—O— or —O—$CH_2$—; and $R^2$ is a substituted or unsubstituted phenyl or naphthyl group; or a nontoxic salt thereof.

4. A method of promoting the oral absorption of insulin, which comprises orally administering concurrently with insulin an adjuvant of the formula:

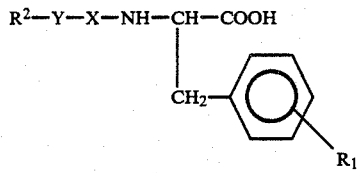

wherein $R^1$ is a hydrogen atom, a fluorine atom, a nitro group, a hydroxyl group or a hydroxyl group protected by an esterifying group; and $R^2$—Y—X is an N-benzyloxycarbonyl-phenylalanyl, an N-benzyloxycarbonyl-4-fluoro-phenylalanyl, or an N-(m-methoxycinnamoyl)-phenylalanyl group; or a nontoxic salt thereof.

5. The orally administratable pharmaceutical composition of claim 1, comprising a mixture of insulin and N-phenoxyacetyl-D-phenylalanine.

6. An orally administratable pharmaceutical composition in dosage unit form suitable for gastrointestinal absorption, comprising a mixture of insulin, and an adjuvant of the formula:

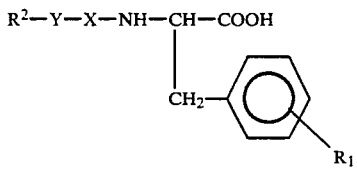

wherein $R^1$ is H; X is CO; Y is a substituted or unsubstituted vinylidene group; and $R^2$ is a phenyl group or a phenyl group substituted by a methyl group, a fluorine atom, a chlorine atom, or a trifluoromethyl group.

7. A method for promoting the absorption of insulin, which comprises orally administering concurrently with insulin an adjuvant of the formula:

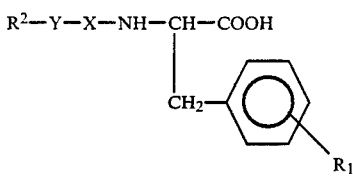

wherein $R^1$ is H; X is CO; Y is a substituted or unsubstituted vinylene group; and $R^2$ is a phenyl group or a phenyl group substituted by a methyl group, a fluorine atom, a chlorine atom, or a trifluoromethyl group.

8. The orally administratable pharmaceutical composition of claim 1, comprising a mixture of insulin and N-[(1-naphthoxy)acetyl]-L-phenylalanine.

9. The orally administratable pharmaceutical composition of claim 1, comprising a mixture of insulin and N-[(2-naphthoxy)acetyl]-L-phenylalanine.

10. The orally administratable pharmaceutical composition of claim 2, comprising a mixture of insulin and N-benzyloxycarbonyl-L-phenylalanyl-L-phenylalanine.

11. The orally administratable pharmaceutical composition of claim 6, comprising a mixture of insulin and N-(4-methylcinnamoyl)-L-phenylalanine.

12. The method of promoting the absorption of insulin of claim 3, which comprises orally administering, concurrently with a unit dosage amount of insulin and N-phenoxyacetyl-D-phenylalanine.

13. The method of promoting the absorption of insulin of claim 3, which comprises orally administering, concurrently with a unit dosage amount of insulin and N-[(1-naphthoxy)acetyl]-L-phenylalanine.

14. The method of promoting the absorption of insulin of claim 3, which comprises orally administering, concurrently with a unit dosage amount of insulin and N-[(2-naphthoxy)acetyl]-L-phenylalanine.

15. The method of promoting the absorption of insulin of claim 4, which comprises orally administering, concurrently with a unit dosage amount of insulin and N-benzyloxycarbonyl-L-phenylalanyl-L-phenylalanine.

16. The method of promoting the absorption of insulin of claim 7, which comprises orally administering, concurrently with a unit dosage amount of insulin and N-(4-methylcinnamoyl)-L-phenylalanine.

17. The orally administratable pharmaceutical composition of claim 1, comprising a mixture of insulin and N-[(4-chlorophenoxy)-acetyl]-L-phenylalanine.

18. The orally administratable pharmaceutical composition of claim 6, comprising a mixture of insulin and N-(α-fluorocinnamoyl)-L-phenylalanine.

19. The method of promoting the absorption of insulin of claim 3, which comprises orally administering, concurrently with a unit dosage amount of insulin and N-[(4-chlorophenoxy)-acetyl]-L-phenylalanine.

20. The method of promoting the absorption of insulin of claim 7, which comprises orally administering, concurrently with a unit dosage amount of insulin and N-(α-fluorocinnamoyl)-L-phenylalanine.

* * * * *